United States Patent [19]
Ben-Nun

[11] Patent Number: 5,858,965
[45] Date of Patent: Jan. 12, 1999

[54] PHARMACEUTICAL COMPOSITIONS FOR THE TREATMENT OF AUTOIMMUNE DISEASES COMPRISING THE B-OLIGOMER OF PERTUSSIS TOXIN OR ITS SUBUNITS

[75] Inventor: Avraham Ben-Nun, Yavne, Israel

[73] Assignee: Yeda Research and Development Co. Ltd., Rehovot, Israel

[21] Appl. No.: 849,376

[22] PCT Filed: Dec. 4, 1995

[86] PCT No.: PCT/US95/16450

§ 371 Date: Jul. 30, 1997

§ 102(e) Date: Jul. 30, 1997

[87] PCT Pub. No.: WO96/17620

PCT Pub. Date: Jun. 13, 1996

[30] Foreign Application Priority Data

Dec. 4, 1994 [IL] Israel .......................................... 111866

[51] Int. Cl.[6] ........................... A61K 38/16; A61K 39/10
[52] U.S. Cl. ....................... 514/2; 424/190.1; 424/240.1; 530/350; 530/825
[58] Field of Search .............................. 424/190.1, 240.1; 514/2, 12; 530/350, 825

[56] References Cited

U.S. PATENT DOCUMENTS

| | | | |
|---|---|---|---|
| 4,845,036 | 7/1989 | Burns et al. | 435/194 |
| 5,453,272 | 9/1995 | Heerze et al. | 424/190.1 |

FOREIGN PATENT DOCUMENTS

| | | |
|---|---|---|
| 58-059925 | 4/1983 | Japan . |
| 92/19646 | 11/1992 | WIPO . |

OTHER PUBLICATIONS

Nencioni et al., "Properties of the B Oligomer of Pertussis Toxin,", Infection And Immunity, vol. 59, No. 12, pp. 4732–4734 (Dec. 1991).

Tamura et al., "A Role of the B–Oligomer Moiety of Islet–activating Protein, Pertussis Toxin, in development of the Biological Effects on Intact Cells." THE Journal Of Biological Chemistry, vol. 258, No. 11, pp. 6756–6761 (10 Jun. 1983).

Ben–Nun et al., "Protection Against Autoimmune Disease by Bacterial Agents II. PPD and Pertussis Toxin as Proteins Active in Protecting Mice Against Expiramental Autoimmune Encephalomyelitis." Eur. J. Immunol., vol. 23, No. 3, pp. 689–696 (1993).

W.J. Black et al., "ADP–Ribosyltransferase Activity of Pertussis Toxin and Immunomodulation by Bordetella Pertussis", Science, vol. 240, pp. 656–659, Apr. 29, 1988.

W. Neal Burnette et al., "Direct Expression of Bordetella Pertussis Toxin Subunits to High Levels in *Escherichia Coli*", Bio/Technology, vol. 6, pp. 699–706, Jun., 1988.

Drusilla L. Burns et al., "Role of the A Subunit of Pertussis Toxin in Alteration of Chinese Hamster Ovary Cell Morphology", Infection and Immunity, vol. 55, No. 1, pp. 24–28, Jan., 1987.

P. Gierschik, "Guanine Nucleotide–Binding Proteins by Pertussis Toxin", Current Topics in Microbiology and Immunology, vol. 175, pp. 69–96, 1992.

Dan Lehmann et al., "Bacterial Agents Protect Against Autoimmune Disease. I. Mice Pre–Exposed to Bordetella Pertussis or Mycobacterium Tuberculosis are Highly Refractory to Induction of Experimental Autoimmune Encephalomyelitis", Journal of Autoimmunity, vol. 5, pp. 675–690, 1992.

(List continued on next page.)

*Primary Examiner*—Jeffrey E. Russel
*Attorney, Agent, or Firm*—Browdy and Neimark

[57] ABSTRACT

The invention provides the use of a protein selected from the B-oligomer of pertussis toxin, an individual subunit S2, S3, S4 or S5 thereof, or a combination of the subunits, for the preparation of pharmaceutical compositions comprising them for the treatment of autoimmune diseases.

9 Claims, 7 Drawing Sheets

OTHER PUBLICATIONS

D. Scott Linthicum et al., "Acute Experimental Autoimmune Encephalomyelitis in Mice", Cellular Immunology, vol. 73, pp. 299–310, 1982.

Alfredo Nicosia et al., "Cloning and Sequencing of the Pertussis Toxin genes: Operon Stucture and Gene Duplication", Proc. Natl. Acad. Sci. USA, vol. 83, pp. 4631–4635, Jul. 1986.

Camille Locht et al., "Pertussis Toxin Gene: Nucleotide Sequence and Genetic Organization", Science, vol. 232, pp. 1258–1264, 1986.

A. Nicosia et al., "Expression and Immunological Properties of the Five Subunits of Pertussis Toxin", Infection and Immunity, vol. 55, pp. 963–967, Apr. 1987.

Makoto Tamura et al., "Subunit Structure of Islet–Activating Protein, Pertussis Toxin, in Conformity with the A–B Model", Biochemistry, vol. 21, pp. 5516–5522, 1982.

FIG. 1

```
  1  TCC ACG CCA GGC ATC GTC ATT CCG CCG CAG GAA CAG ATT ACC CAG  45
     Ser Thr Pro Gly Ile Val Ile Pro Pro Gln Glu Gln Ile Thr Gln
                       5                  10                  15

46  CAT GGC AGC CCC TAT GGA CGC TGC GCG AAC AAG ACC CGT GCC CTG  90
     His Gly Ser Pro Tyr Gly Arg Cys Ala Asn Lys Thr Arg Ala Leu
                      20                  25                  30

91  ACC GTG GCG GAA TTG CGC GGC AGC GGC GAT CTG CAG GAG TAC CTG 135
     Thr Val Ala Glu Leu Arg Gly Ser Gly Asp Leu Gln Glu Tyr Leu
                      35                  40                  45

136  CGT CAT GTG ACG CGC GGC TGG TCA ATA TTT GCG CTC TAC GAT GGC 180
     Arg His Val Thr Arg Gly Trp Ser Ile Phe Ala Leu Tyr Asp Gly
                      50                  55                  60

181  ACC TAT CTC GGC GGC GAA TAT GGC GGC GTG ATC AAG GAC GGA ACA 225
     Thr Tyr Leu Gly Gly Glu Tyr Gly Gly Val Ile Lys Asp Gly Thr
                      65                  70                  75

226  CCC GGC GGC GCA TTC GAC CTG AAA ACG ACG TTC TGC ATC ATG ACC 270
     Pro Gly Gly Ala Phe Asp Leu Lys Thr Thr Phe Cys Ile Met Thr
                      80                  85                  90

271  ACG CGC AAT ACG GGT CAA CCC GCA ACG GAT CAC TAC TAC AGC AAC 315
     Thr Arg Asn Thr Gly Gln Pro Ala Thr Asp His Tyr Tyr Ser Asn
                      95                 100                 105

316  GTC ACC GCC ACT CGC CTG CTC TCC AGC ACC AAC AGC AGG CTA TGC 360
     Val Thr Ala Thr Arg Leu Leu Ser Ser Thr Asn Ser Arg Leu Cys
                     110                 115                 120

361  GCG GTC TTC GTC AGA AGC GGG CAA CCG GTC ATT GGC GCC TGC ACC 405
     Ala Val Phe Val Arg Ser Gly Gln Pro Val Ile Gly Ala Cys Thr
                     125                 130                 135

406  AGC CCG TAT GAC GGC AAG TAC TGG AGC ATG TAC AGC CGG CTG CGG 450
     Ser Pro Tyr Asp Gly Lys Tyr Trp Ser Met Try Ser Arg Leu Arg
                     140                 145                 150

451  AAA ATG CTT TAC CTG ATC TAC GTG GCC GGC ATC TCC GTA CGC GTC 495
     Lys Met Leu Tyr Leu Ile Tyr Val Ala Gly Ile Ser Val Arg Val
                     155                 160                 165

496  CAT GTC AGC AAG GAA GAA CAG TAT TAC GAC TAT GAG GAC GCA ACG 540
     His Val Ser Lys Glu Glu Gln Tyr Tyr Asp Tyr Glu Asp Ala Thr
                     170                 175                 180

541  TTC GAG ACT TAC GCC CTT ACC GGC ATC TCC ATC TGC AAT CCT GGA 585
     Phe Glu Thr Tyr Ala Leu Thr Gly Ile Ser Ile Cys Asn Pro Gly
                     185                 190                 195

586  TCA TCC TTA TGC                                              597
     Ser Ser Leu Cys
                 199
```

FIG. 2

```
  1  GTT GCG CCA GGC ATC GTC ATC CCG CCG AAG GCA CTG TTC ACC CAA  45
     Val Ala Pro Gly Ile Val Ile Pro Pro Lys Ala Leu Phe Thr Gln
                   5               10                      15

46  CAG GGC GGC GCC TAT GGA CGC TGC CCG AAC GGA ACC CGC GCC TTG  90
     Gln Gly Gly Ala Tyr Gly Arg Cys Pro Asn Gly Thr Arg Ala Leu
                  20               25                      30

91  ACC GTG GCC GAA CTG CGC GGC AAC GCC GAA TTG CAG ACG TAT TTG 135
     Thr Val Ala Glu Leu Arg Gly Asn Ala Glu Leu Gln Thr Tyr Leu
                  35               40                      45

136  CGC CAG ATA ACG CCC GGC TGG TCC ATA TAC GGT CTC TAT GAC GGT 180
     Arg Gln Ile Thr Pro Gly Trp Ser Ile Tyr Gly Leu Tyr Asp Gly
                  50               55                      60

181  ACG TAC CTG GGC CAG GCG TAC GGC GGC ATC ATC AAG GAC GCG CCG 225
     Thr Tyr Leu Gly Gln Ala Tyr Gly Gly Ile Ile Lys Asp Ala Pro
                  65               70                      75

226  CCA GGC GCG GGG TTC ATT TAT CGC GAA ACT TTC TGC ATC ACG ACC 270
     Pro Gly Ala Gly Phe Ile Tyr Arg Glu Thr Phe Cys Ile Thr Thr
                  80               85                      90

271  ATA TAC AAG ACC GGG CAA CCG GCT GCG GAT CAC TAC TAC AGC AAG 315
     Ile Tyr Lys Thr Gly Gln Pro Ala Ala Asp His Tyr Tyr Ser Lys
                  95              100                     105

316  GTC ACG GCC ACG CGC CTG CTC GCC AGC ACC AAC AGC AGG CTG TGC 360
     Val Thr Ala Thr Arg Leu Leu Ala Ser Thr Asn Ser Arg Leu Cys
                 110              115                     120

361  GCG GTA TTC GTC AGG GAC GGG CAA TCG GTC ATC GGA GCC TGC GGC 405
     Ala Val Phe Val Arg Asp Gly Gln Ser Val Ile Gly Ala Cys Ala
                 125              130                     135

406  AGC CCG TAT GAA GGC AGG TAC AGA GAC ATG TAC GAC GCG CTG CGG 450
     Ser Pro Tyr Glu Gly Arg Tyr Arg Asp Met Tyr Asp Ala Leu Arg
                 140              145                     150

451  CGC CTG CTG TAC ATG ATC TAT ATG TCC GGC CTT GCC GTA CGC GTC 495
     Arg Leu Leu Tyr Met Ile Tyr Met Ser Gly Leu Ala Val Arg Val
                 155              160                     165

496  CAC GTC AGC AAG GAA GAG CAG TAT TAC GAC TAC GAG GAC GCC ACA 540
     His Val Ser Lys Glu Glu Gln Tyr Tyr Asp Tyr Glu Asp Ala Thr
                 170              175                     180

541  TTC CAG ACC TAT GCC CTC ACC GGC ATT TCC CTC TGC AAC CCG GCA 585
     Phe Gln Thr Tyr Ala Leu Thr Gly Ile Ser Leu Cys Asn Pro Ala
                 185              190                     195

586  GCG TCG ATA TGC    597
     Ala Ser Ile Cys
                 199
```

FIG. 3

```
  1  GAC GTT CCT TAT GTG CTG GTG AAG ACC AAT ATG GTG GTC ACC AGC   45
     Asp Val Pro Tyr Val Leu Val Lys Thr Asn Met Val Val Thr Ser
                      5                  10                  15

46  GTA GCC ATG AAG CCG TAT GAA GTC ACC CCG ACG CGC ATG CTG GTC   90
     Val Ala Met Lys Pro Tyr Glu Val Thr Pro Thr Arg Met Leu Val
                     20                  25                  30

91  TGC GGC ATC GCC GCC AAA CTG GGC GCC GCG GCC AGC AGC CCG GAC  135
     Cys Gly Ile Ala Ala Lys Leu Gly Ala Ala Ala Ser Ser Pro Asp
                     35                  40                  45

136  GCG CAC GTG CCG TTC TGC TTC GGC AAG GAT CTC AAG CGT CCC GGC  180
     Ala His Val Pro Phe Cys Phe Gly Lys Asp Leu Lys Arg Pro Gly
                     50                  55                  60

181  AGC AGT CCC ATG GAA GTC ATG TTG CGC GCC GTC TTC ATG CAA CAA  225
     Ser Ser Pro Met Glu Val Met Leu Arg Ala Val Phe Met Gln Gln
                     65                  70                  75

226  CGG CCG CTG CGC ATG TTT CTG GGT CCC AAG CAA CTC ACT TTC GAA  270
     Arg Pro Leu Arg Met Phe Leu Gly Pro Lys Gln Leu Thr Phe Glu
                     80                  85                  90

271  GGC AAG CCC GCG CTC GAA CTG ATC CGG ATG GTC GAA TGC AGC GGC  315
     Gly Lys Pro Ala Leu Glu Leu Ile Arg Met Val Glu Cys Ser Gly
                     95                 100                 105

316  AAG CAG GAT TGC CCC                                           330
     Lys Gln Asp Cys Pro
                    110
```

FIG. 4

```
  1  GCC GGC TTG CCG ACC CAT CTG TAC AAG AAC TTC ACT GTC CAG GAG   45
     Ala Gly Leu Pro Thr His Leu Tyr Lys Asn Phe Thr Val Gln Glu
                      5                  10                  15

46  CTG GCC TTG AAA CTG AAG GGC AAG AAT CAG GAG TTC TGC CTG ACC   90
     Leu Ala Leu Lys Leu Lys Gly Lys Asn Gln Glu Phe Cys Leu Thr
                     20                  25                  30

91  GCC TTC ATG TCG GGC AGA AGC CTG GTC CGG GCG TGC CTG TCC GAC  135
     Ala Phe Met Ser Gly Arg Ser Leu Val Arg Ala Cys Leu Ser Asp
                     35                  40                  45

136  GCG GGA CAC GAG CAC GAC ACG TGG TTC GAC ACC ATG CTT GGC TTT  180
     Ala Gly His Glu His Asp Thr Trp Phe Asp Thr Met Leu Gly Phe
                     50                  55                  60

181  GCC ATA TCC GCG TAT GCG CTC AAG AGC CGG ATC GCG CTG ACG GTG  225
     Ala Ile Ser Ala Tyr Ala Leu Lys Ser Arg Ile Ala Leu Thr Val
                     65                  70                  75

226  GAA GAC TCG CCG TAT CCG GGC ACT CCC GGC GAT CTG CTC GAA CTG  270
     Glu Asp Ser Pro Tyr Pro Gly Thr Pro Gly Asp Leu Leu Glu Leu
                     80                  85                  90

271  CAG ATC TGC CCG CTC AAC GGA TAT TGC GAA   300
     Gln Ile Cys Pro Leu Asn Gly Tyr Cys Glu
                     95                 100
```

PHARMACEUTICAL COMPOSITIONS FOR THE TREATMENT OF AUTOIMMUNE DISEASES COMPRISING THE B-OLIGOMER OF PERTUSSIS TOXIN OR ITS SUBUNITS

FIELD OF THE INVENTION

The present invention is generally in the field of agents that may be used for the treatment of autoimmune diseases, and more particularly relates to pharmaceutical compositions comprising the B-oligomer of pertussis toxin or one of its subunits S2, S3, S4 or S5, or combinations thereof, useful for protection against autoimmune diseases.

BACKGROUND OF THE INVENTION

The gram-negative bacterium Bordetella pertussis (B. pertussis), the causative agent of whooping cough, produces several virulence factors. Pertussis toxin (PT), the major virulence component of B. pertussis, appears to contain an important epitope that leads to the formation of antibodies capable of protecting against the disease. Therefore, PT has been extensively investigated with regard to its possible use in preparing vaccines for whooping cough (Black et al., 1988).

Pertussis toxin is a 105-kDa hexameric protein composed of five distinct non-covalently linked polypeprides designated (in the order of decreasing molecular weight) S1–S5.PT can be divided into two distinct functional units, the enzymatically active toxic A-protomer, consisting of a single polypeptide (S1), and the pentameric B-oligomer (S2, S3, two copies of S4, and S5, i.e. molar ratio1:1:2:1). The B-oligomer is responsible for binding of the toxin to the surface of eukaryotic target cells. The two S4 polypeptides form two distinct heterodimers with S2 and S3, which are in turn held together by S5 (see review by Gierschik, 1992).

The perrussis toxin gene has been cloned and sequenced (Nicosia et al., 1986; European Patent Application EP 0232 229; Locht and Keith, 1986; U.S. Pat. No. 4, 883,761). The individual subunits have been subcloned and expressed in E. coli in nonfusion form (Burnette et al.,1988) or as fusion proteins (Nicosia et al., 1987), and tested as antigens for protection against whooping cough.

The development of experimental autoimmune encephalomyelitis (EAE), as well as other autoimmune diseases in experimental animals, can be facilitated by injecting Bordetella pertussis concomitantly with inoculation of the autoantigen (Bernard et al., 1992). EAE is a neurological autoimmune disease which can be induced in experimental animals by a single injection of central nervous system (CNS) tissue homogenate or purified myelin antigens such as myelin basic protein (MBP) or proteolipid protein (PLP) in complete Freund's adjuvant (CFA) (Tabira and Kira, 1992). The clinical and pathological features of EAE are reminiscent of multiple sclerosis, and EAE is a well-accepted model for multiple sclerosis. In mice,. consistent elicitation of EAE was shows to be facilitated by administration of B. pertussis at the time of the encephalitogenic challenge (Munoz, 1985). Pertussis toxin (PT) was shown later to be the component of B. pertussis responsible for facilitating disease development, and it is now routinely used in place of B. pertussis for enhancement of autoimmune disease in experimental animals (Munoz, 1995).

In an analysis of the possible inununomodulating activity of various bacteria, it was found by the present inventor that B. pertussis not only enhances the development of EAE in mice, but can also protect against the disease depending on the time and route of injection (Lehman and Ben-Bun, 1993). The protective activity of B. pertussis was subsequently assigned to PT (Ben-Nun et al., 1993).

Pertussis toxin (PT), the major virulence determinant of B. pertussis, is composed of two distinct functional units: the A-protomer consisting of a single polypeptide (S1) that mediates adenosine diphosphate (ADP)-ribosylation of host G proteins, and the B-oligomer, a complex pentamer composed of subunits S2, S3, S4 and S5 in a respective molar ratio of 1:1:2:1, which mediates the binding of the toxin to host tissue by interaction with glycoproteins and glycolipids on many types of eukaryotic cells (Gierschik, 1992). PT was found to have mitogenic and immunoadjuvant properties (Munoz, 1985). The mechanism by which PT can enhance the development of EAE in mice is not yet clear. However, it has been suggested that PT facilitates the access of autoantigen-specific T cells to the CNS by affecting the vascular permeability of the blood-brain barrier (Linthicum et al., 1982).

The mechanism by which PT protects against the development of EAE is also unclear. To further understand how both enhancing and protective activities are mediated by the same, albeit complex, molecule, it is essential to delineate the regions of the PT holomer which may be associated with one or both of these activities.

SUMMARY OF THE INVENTION

It has now been found in accordance with the present invention that the B-oligomer of pertussis toxin or a subunit S2, S3, S4 or S5 thereof, are able to block the development of EAE in mice. Since EAE is a well-established and widely accepted animal model for the study of autoimmune diseases, these findings indicate that the B-oligomer of pertussis toxin or a subunit S2, S3, S4 or S5 thereof, will be useful for the protection against autoimmune diseases in humans.

The present invention thus relates to a pharmaceutical composition comprising as active ingredient the B-oligomer of pertussis toxin or an individual subunit S2, S3, S4 or S5 thereof, or a combination of said subunits, and a pharmaceutically acceptable carrier, useful for protection against autoimmune diseases in humans.

Any autoimmune disease can be treated with a pharmaceutical composition of the invention, such as rheumatoid arthritis, systemic lupus erythematosus, insulin-dependent diabetes mellitus and graft-versus-host disease, and more particularly, multiple sclerosis.

The invention also relates to the use of the B-oligomer of perrussis toxin or an individual subunit S2, S3, S4 or S5 thereof, or a combination of said subunits, for the manufacture of a pharmaceutical composition useful for the protection against autoimmune diseases in humans.

Also encompassed by the present invention is a method for the treatment of a patient afflicted with an autoimmune disease which comprises administering to such a patient an effective amount of the B-oligomer of pertussis toxin or an individual subunit S2, S3, S4 or S5 thereof, or a combination of said subunits.

DESCRIPTION OF THE FIGURES

FIG. 1 depicts the nucleotide and amino acid sequence of the subunit S2 of the B-oligomer of pertussis toxin (SEQ ID NOS:1 and 2).

FIG. 2 depicts the nucleotide and amino acid sequence of the subunit S3 of the B-oligomer of pertussis toxin (SEQ ID NOS:3 and 4).

FIG. 5 shows protection against the development of EAE by PT administered in oil or in aqueous solution. PT (400 ng) in 0.1 ml emulsion of IFA or in aqueous solution (PBS) was injected s.c. in the flanks, 18 days prior to the encephalitogenic challenge. X denotes mortality of all mice in the group. P and M represent incidence of paralysis and mortality, respectively, in each group. a) p=0.0002, and b) p=0.0012, when compared to P or M, respectively, in the combined controls (None+IFA).

FIG. 6 shows that the B-oligomer blocks the development of EAE. B-oligomer (100 ng) or PT (400 ng) emulsified in IFA were injected s.c. 16 days prior to the encephalitogenic challenge. a) p=0.001, and b) p=0.001 when compared to P or M, respectively, in the combined controls (None+IFA).

FIG. 8 shows differential protective effect of the B-oligomer subunits. 100 ng of B-oligomer or of gel-purified subunits were emulsified in IFA and injected s.c. 20 days before the encephalitogenic challenge. a) p=0.0002, b) p=0.0043, c) p=0.0016, and d) p=0.014 when compared to P in the combined controls (None+IFA); e) p=0.001, f) p=0.008 and g) p=0.04 when compared to M in the combined controls (None+IFA).

DETAILED DESCRIPTION OF THE INVENTION

PT administered in oil or in aqueous solution protects mice against the development of EAE (FIG. 5), which is routinely used as a model for organ-specific T-cell mediated autoimmune diseases, suggesting its potential efficacy for therapy of such diseases. However, the use of PT as a therapeutic agent is rather risky in view of its toxicity.

In order to identify regions of PT associated with enhancement or with blocking of disease, both for potential therapeutic use and for a better understanding of the mechanisms of action of PT on autoimmune diseases, the effect of the constitutive units of PT on the development of EAE was investigated according to the present invention. The findings showm herein in the examples that the B-oligomer of PT, which does not contain the toxic S1 monomer, has a remarkable protective effect against EAE (FIG. 6), indicate that the B-oligomer is responsible for the protective activity of PT. Furthermore, the failure of the B-oligomer to enhance the development of EAE (FIG. 9) indicates that the enhancement of autoimmune diseases by PT is likely to be associated with the S1 monomer of PT.

Several features of the B-oligomer of PT make it a potentially useful agent for the therapy of autoimmune diseases: i) it is highly potent in blocking the development of EAE; ii) it is devoid of the enhancing activity of PT; and iii) the B-oligomer, which does not comprise the toxic S1 monomer, is non-toxic in vivo.

The subunits S2, S3, S4 and S5 of the B-oligomer were purified (FIG. 7) and tested for their ability to protect against EAE, in the attempt to assign the protective activity of the B-oligomer to a particular subunit. The findings that each subunit has protective activity (FIG. 8) further indicate that each can be used as a therapeutic agent for autoimmune diseases. Each subunit protected against EAE to a different extent, and the protection conferred was not as complete as that given by the B-oligomer, indicating that various combinations of the subunits in the form of mixtures, e.g. S2+S3, S2+S4, S2+S3+S5, or as heterodimers, e.g. S2/S4, S3/S4, may be more effective in abolishing disease development.

Hence, the B-oligomer of PT and the subunits of the B-oligomer, individually or in various combinations, are potentially useful agents for the therapy of multiple sclerosis and other autoimmune diseases, such as rheumatoid arthritis, insulin-dependent diabetes mellitus, systemic lupus erythematosus, and graft-versus-host disease.

In preferred embodiments, the pharmaceutical compositions of the invention comprise as active ingredient the B-oligomer, the subunit S2 or S3, a mixture of S2 and S3, or of S2, S3 and S5, or a heterodimer S2/S4 or S3/S4, or a mixture of said heterodimers.

The B-oligomer of PT is commercially available or can be prepared by any method described in the art, such as for example by dissociation of pertussis toxin into the A protomer and the B-oligomer by affinity chromatography (Tamura et al., 1982; and 1983; Bums et al., 1987), or by combining heterodimer S2/S4, heterodimer S3/S4 and subunit S5 at the 1:1:1 molar ratio in 2M urea (Tamura et al., 1983). All attempts to prepare recombinant B-oligomer have not been successful.

The individual subunits S2, S3, S4 and S5, both native and recombinant, are encompassed by the invention. The native subunits can be prepared, for example, by preparative gel electrophoresis as described according to the present invention (FIG. 7) or by gel filtration (Tamura et al., 1982), and the recombinant subunits as described by Nicosia et al, 1987, and Burnette et al., 1988. The heterodimers S2/S4 and S3/S4 are also prepared according to Tamura et al., 1982.

The pharmaceutical compositions of the invention comprise a pharmaceutically acceptable carrier and as active ingredient the B-oligomer of PT or an individual subunit S2, S3, S4 or S5 thereof, or a combination of said subunits. By "combination" of said subunits it is herein included both mixtures of the subunits, for example a mixture of S2 and S3, or S2 and S4, or a heterodimer S2/S4 and S3/S4 associated similarly to the native molecule, or a mixture of said heterodimers.

The pharmaceutical compositions are prepared by mixing the active ingredient with a pharmaceutically acceptable carrier, stabilizers and excipients, and prepared in dosage form, e.g. by lyophilization in dosage vials. They may be administered in all suitable ways, e.g. intravenously, intramuscularly, subcutaneously, local injection, topical application or per os, as the case may require. The amount of active compound to be administered will depend on the route of administration, the disease to be treated and the condition of the patient.

The invention will now be described in more detail in the following non-limiting examples and their accompanying figures.

EXAMPLES

Materials and Methods (a) Materials

Pertussis toxin (PT) was obtained from Sigma (St Louis, Mo., U.S.A.) and also as a kind gift from Dr. D. Teitelbaum (The Weizmann Institute of Science, Rehovot, Israel). The B-oligomer of PT was obtained from List Biological Laboratories Inc. (Campbell, Calif.).

(b) Mice

Female SJL/J mice were purchased from Jackson Laboratories (Bar Harbor, Me, U.S.A.). All mice were 2–3 months old when used in the experiments.

(c) Induction of EAE

EAE was induced in mice as previously described (Ben-Nun and Lando. 1983). Briefly, 0.1 ml of emulsion prepared from mouse spinal cord homogenate (MSCH, 60 mg/ml) emulsified with an equal volume of CFA enriched for M. tuberculosis H37Ra (5mg/ml) was injected s.c. into the mouse footpads. Immediately after and 48 hrs later, PT was injected intravenously (400 ng/mouse). Where stated in the text. the B-oligomer (400 ng/mouse) was also used in place of PT to evaluate its effect on disease enhancement.

(d) Clinical evaluation, scoring and statistical analysis

Following the encephalitogenic challenge, mice were observed daily for clinical signs of EAE. The severity of the clinical manifestations was scored daily for each individual mouse in the treatment group on a scale of 0–6; 0: no clinical signs, 1: loss of tail tonicity, 2: flaccid tail, 3: hind leg paralysis, 4: hind leg paralysis with hind body paresis, 5: hind and fore leg paralysis, 6: death. Results presented denote the mean score of the treatment group on each given day after encephalitogenic challenge. At the peak of the clinical disease, on days 12–17 after encephalitogenic challenge, the standard errors (not shown) were less than 16% of the mean clinical score. Each graph also displays the incidence of paralysis (P) and mortality (M) for each treatment group in order to allow a complete evaluation of the clinical course of EAE.

To evaluate the statistical significance of the differences in incidence of paralysis or mortality between treatment and control groups in each experiment, the contingency table analysis was used to calculate the $\chi^2$ values with the Stat View 512$^+$program. Due to the relatively small number of mice in each group, the p values given are of $\chi^2$ with continuity correction.

(e) Protection against EAE

For the induction of protection against the disease, mice were injected s.c. in the flanks with 400 ng of PT, or with 100 ng of B-oligomer or gel-eluted subunits of the B-oligomer, emulsified in incomplete Freund's adjuvant (IFA). A total volume of 0.1 ml was injected 2–3 weeks prior to encephalitogenic challenge. Where indicated, PT was injected in aqueous solution (PBS) s.c. in the flanks, in a total volume of 0.1 ml.

Example 1. Effect Of pertussis Toxin on the development of EAE

Figure 3:
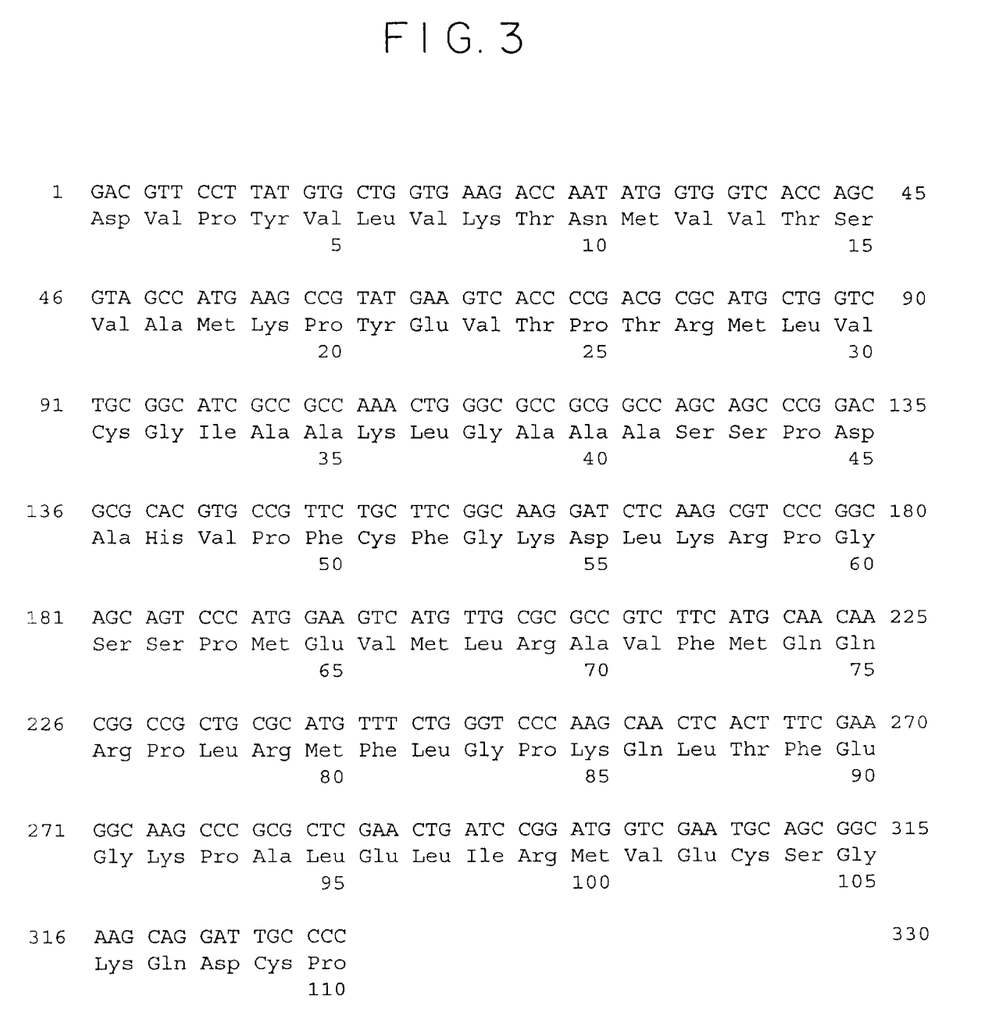
FIG. 3 depicts the nucleotide and amino acid sequence of the subunit S4 of the B-oligomer of pertussis toxin (SEQ ID NOS:5 and 6).
Figure 4:
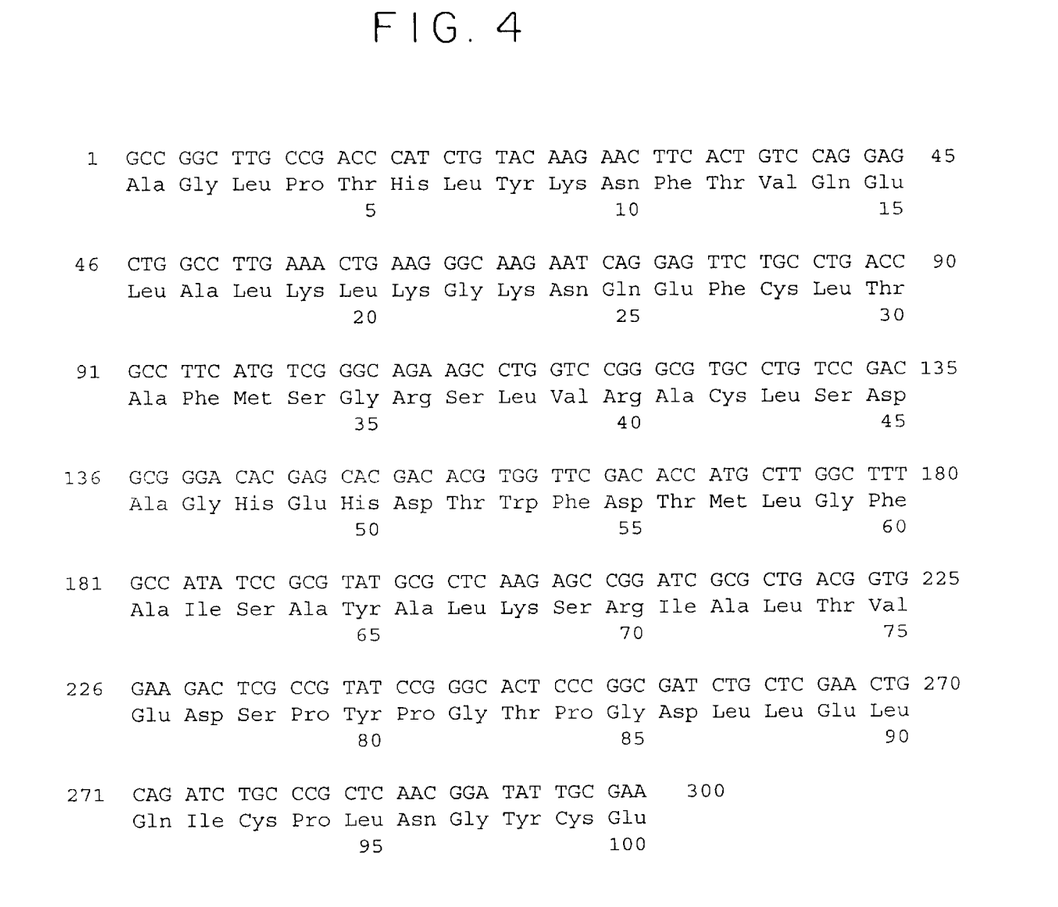
FIG. 4 depicts the nucleotide and amino acid sequence of the subunit S5 of the B-oligomer of pertussis toxin (SEQ ID NOS:7 and 8).
Figure 5:
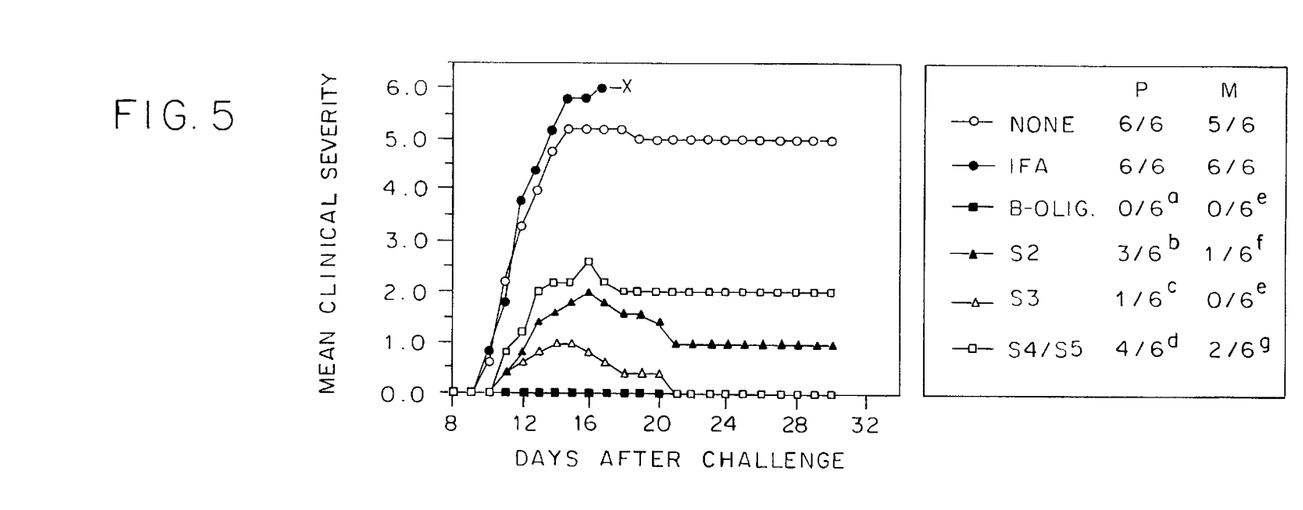

FIG. 5 shows that a single injection of PT prior to the encephalitogenic challenge has a dramatic effect on the subsequent development of EAE induced in SJL/J mice by CNS tissue homogenate. PT was remarkably effective in blocking the development of EAE regardless of whether it was administered s.c. as an oil emulsion or an aqueous solution. These results show that PT can not only facilitate the development of autoimmune diseases as previously shown (Munoz, 1985). but also has a strong protective activity which can completely abolish disease development (Ben-Nun et al., 1993).

Figure 6:
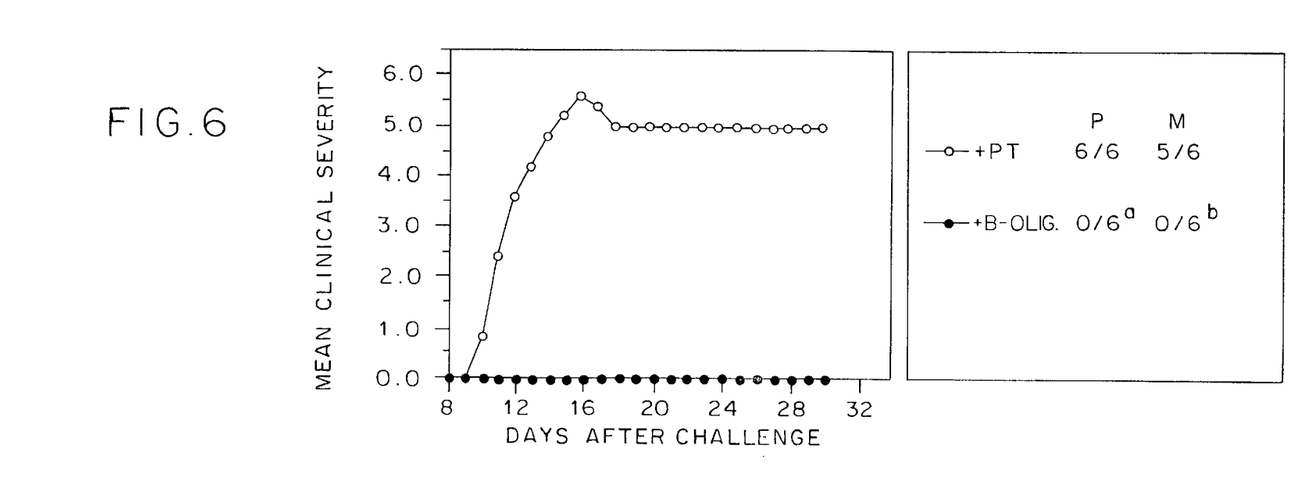

Example 2. Effect of the B-oligomer of pertussis toxin on the development of EAE To identify regions of the PT molecule that can be associated with the enhancing effect or with the protective activity of PT, the A-protomer and the B-oligomer were investigated. FIG. 6 shows that the B-oligomer, which is devoid of the toxic S1 subunit. is sufficient to protect against the development of EAE. The protection against EAE was total with as little as 50–100 ng of B-oligomer per mouse administered as a single injection. B-oligomer was at least as potent as whole PT in protecting mice against the disease.

Figure 7:
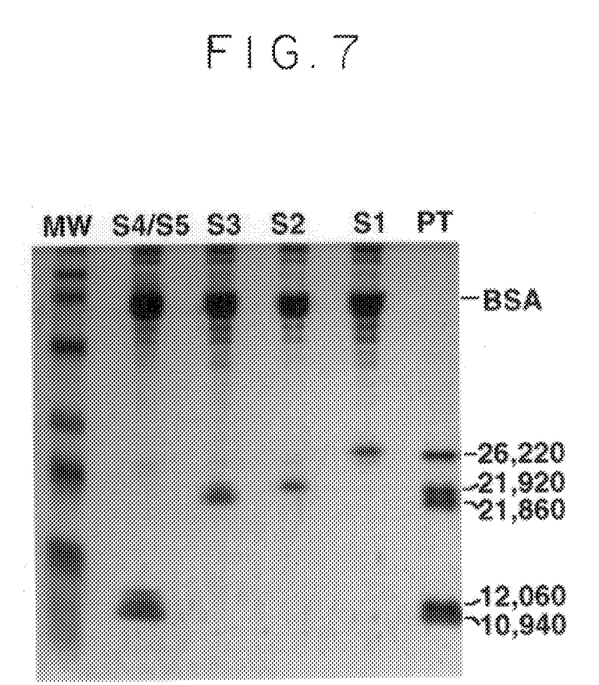
FIG. 7 shows silver-stained SDS-gel of gel-purified PT subunits. The subunits were isolated by preparative gel electrophoresis and analyzed. Five $\mu$g whole PT, 0.4$\mu$g purified S1, 0.3 $\mu$g purified S2, 0.7$\mu$g purified S3 and 1.25$\mu$g purified S4/S5 were run on the relevant lanes.

Example 3. Purification of PT subunits by elution from preparative SDS-gels and their effect on the development of EAE In the attempt to assign the protective activity of PT to a particular subunit of the B-oligomer, PT (Sigma) was electrophoresed on preparative SDS-gel according to Laemmli, 1970. Each subunit was located according to stained reference lane on each gel (FIG. 7). The unstained relevant bands were cut out from the gel. Each subunit was eluted from the crushed gel band by passive diffusion, dialysed extensively against double distilled $H_2O$ in the presence or absence of bovine serum albumin, lyophilised and resuspended in PBS.

Figure 8:
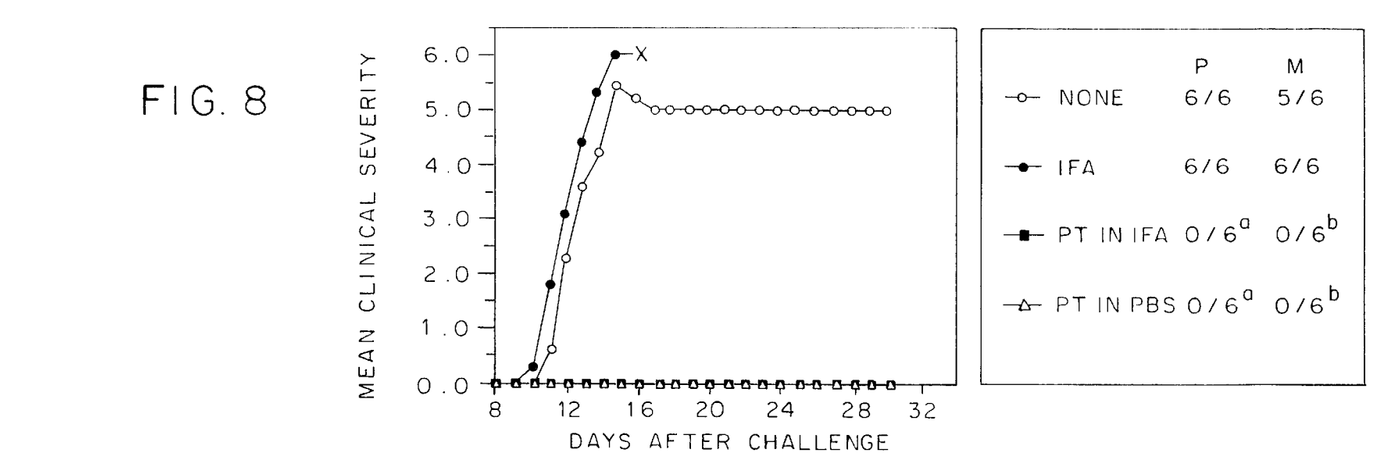

The B-oligomer, subunits S2, S3 and S4/S5 were tested in vivo for protective activity against the development of EAE. As shown in FIG. 8, each of the subunits had a protective effect. However, although the protective activity of the different subunits was marked, the protection was not as total as that obtained with B-oligomer or whole PT.

Example 4. The B-oligomer does not promote development of EAE in mice

Figure 9:
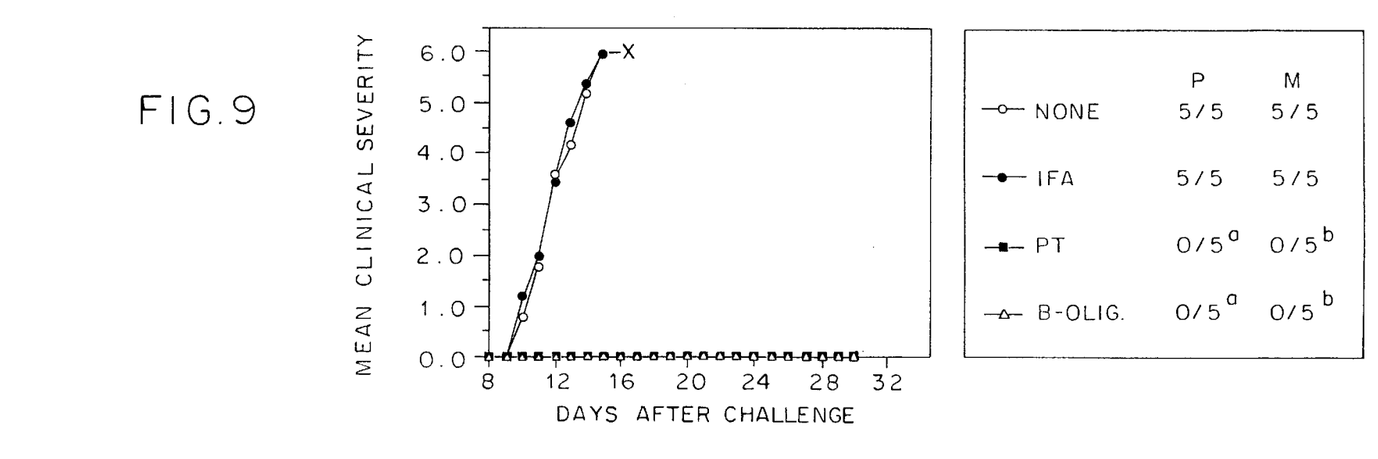
FIG. 9 shows that the B-oligomer does not promote the development of EAE. PT (400 ng) or B-oligomer (400 ng) were injected I.V. immediately, and 48 hours after mice were injected with MSCH/CFA to induce the development of EAE. a) p=0.004, and p=0.02 when compared to P or M, respectively, in the +PT group.

As mentioned above, PT has a conflicting immunomodulatory effect on autoimmune diseases (Ben-Nun et al., 1993). It can facilitate the development of the disease and also protect against it (as shown here). As the B-oligomer was found to be highly effective in protecting against EAE, its possible enhancing effect on the disease was investigated. FIG. 9 shows that in comparison with PT, that facilitated the development of a disease with severe neurological impairment and high mortality, the B-oligomer had no enhancing effect. Thus, all mice that received PT concomitantly with the encephalitogenic challenge developed severe EAE. whilst all mice that received PBS or B-oligomer remained healthy.

References

1. Ben-Nun, A. and Z. Lando. 1983. Detection of cells responding to myelin basic protein by proliferation and selection of T cell lines functional in mediating experimental autoimmune encephalomyelitis (EAE) in mice. *J. Immunol.* 130:1205.
2. Ben-Nun, A., S. Yossefi and D. Lehman. 1993. Protection against autoimmune disease by bacterial agents. II. PPD and pertussis toxin as proteins active in protecting mice against experimental autoimmune encephalomyelitis. *Eur. J Immunol.* 23:689.
3. Bernard, C. C. A., Mandel, T. E. and Mackay, I. R. 1992. Experimental models of human autoimmune diseases: Overview and prototypes. In *The autoimmune diseases II*, Rose, N. and Mackay, I. R. (eds), Academic Press, N.Y., p. 47.
4. Black, W. J., Munoz, J. J., Peacock, M. J., Schad, P. A., Cowell, J. L., Burchall, J. J., Lim, M., Kent, A., Steinman, L. and Falkow, S. 1988. ADP-ribosyltransferase activity of pertussis toxin and immunomodulation by Bordetella perrussis. *Science* 240:656.
5. Burette. W. N. et al. 1988. Direct expression of Bordetella pertussis toxin subunits to high levels in *Escherichia coli*. *Bio/Technology* 6:699–706.
6. Burns, D. L. et al. 1987. Role of the A Subunit of Pertussis Toxin in Alteration of Chinese Hamster Ovary Cell Morphology. *Infection and Immunity* 55:24–28.

7. Gierschik. P. 1992. Guanine Nucleotide-Binding Proteins by Pertussis Toxin. *Current Topics in Microbiology and Immunology*, Springer-Verlag, Berlin, 175:69–96.
8. Laemmli. U. K. 1970. Cleavage of structural proteins during the assembly of the head of bacteriophage T4. *Nature* (Lond.). 227:680.
9. Lehman, D. and A. Ben-Nun. 1992. Bacterial agents protect against autoimmune disease. I. Mice pre-exposed to Bordetella perrussis or Mycobacterium tuberculosis are highly refractory to induction of experimental autoimmune encephalomyelitis. *J. Autoimmune.* 5:675.
10. Linthicum. D. S., Munoz, J. J. and Blaskett, S. 1982. Acute experimental autoimmune encephalomyelitis in mice. I Adjuvant action of *Bordetella pertussis* is due to vasoactive amine sensitization and increased vascular permeability of the central nervous system. *Cell Immunol.* 73:299
11. Locht, C. and Keith, J. M. 1986. Pertussis Toxin Gene: Nucleotide Sequence and Genetic Organization. *Science*. 232:1258–1264.
12. Munoz. J. J. 1985. *In Pertussis toxin*, Sekura, R. D., Moss, J. and Vaughan, M. (eds), Academic Press, N.Y. p. 1.
13. Nicosia, A. et al. 1986. Cloning and sequencing of the pertussis toxin genes: Operon structure and gene duplication. *Proc. Natl. Acad Sci. USA*. 83:4631–4635.
14. Nicosia, A. et al. 1987. Expression and Immunological Properties of the Five Subunits of Pertussis Toxin. *Infection and Immunity*. 55:963–967.
15. Tabira, T. and J.-I. Kira. 1992. Strain and species differences of encephalitogenic determinants of myelin basic protein and proteolipid apoprotein. In Myelin: *Biology and chemistry*, R. E. Martenson, ed. CRC Press, USA. p.783.
16. Tamura, M. et al. 1982. Subunit Structure of Islet-Activating Protein, Pertussis Toxin, in Conformity with the A-B Model. *Biochemistry*. 21:5516–5522.
17. Tamura, M. et al. 1987. A Role of the B-Oligomer Moiety of Islet Activating. Protein, pertussis Toxin, in the Development of the Biological Effects on Intact Cells. *J Biol. Chem*. 258:6756–6761.

I claim:

1. A pharmaceutical composition for the treatment of autoimmune diseases comprising, as active ingredient, the S2/S4 heterodimer of the B-oligomer of pertussis toxin (PT), the S3/S4 heterodimer of the B-oligomer of PT, or a mixture of both heterodimers, in an amount effective for treating autoimmune diseases, and a pharmaceutically acceptable carrier.

2. A pharmaceutical composition according to claim 1 for the treatment of an autoimmune disease selected from the group consisting of multiple sclerosis, rheumatoid arthritis, systemic lupus erythematosus, insulin-dependent diabetes mellitus and graft-versus-host disease.

3. A pharmaceutical composition according to claim 1 wherein the active ingredient is said S3/S4 heterodimer.

4. A method for the treatment of a patient afflicted with an autoimmune disease which comprises administering to said patient an effective amount of a material selected from the group consisting of the S2/S4 heterodimer of the B-oligomer of pertussis toxin (PT), the S3/S4 heterodimer of the B-oligomer of PT, and a mixture of both heterodimers.

5. A method according to claim 4, wherein the autoimmune disease is selected from the group consisting of multiple sclerosis, rheumatoid arthritis, systemic lupus erythematosus, insulin-dependent diabetes mellitus and graft- versus-host disease.

6. A method according to claim 5, wherein the autoimmune disease is multiple sclerosis.

7. A method in accordance with claim 4, wherein said material is said S3/S4 heterodimer.

8. A method in accordance with claim 5, wherein said material is said S3/S4 heterodimer.

9. A method in accordance with claim 6, wherein said material is said S3/S4 heterodimer.

* * * * *

UNITED STATES PATENT AND TRADEMARK OFFICE
CERTIFICATE OF CORRECTION

PATENT NO. : 5,858,965
DATED : January 12, 1999
INVENTOR(S) : Avraham Ben-Nun It is certified that error appears in the above-identified patent and that said Letters Patent is hereby corrected as shown below:

<u>Drawings,</u>
Sheet 5 of 7, delete "FIG. 5" and insert therefor -- FIG. 8 --.
Sheet 5 of 7, delete "FIG. 6" and insert therefor -- FIG. 9 --.
Sheet 7 of 7, delete "FIG. 8" and insert therefor -- FIG. 5 --.
Sheet 7 of 7, delete "FIG. 9" and insert therefor -- FIG. 6 --.

Signed and Sealed this

Sixteenth Day of November, 2004

JON W. DUDAS
*Director of the United States Patent and Trademark Office*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 597 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: CDS
        ( B ) LOCATION: 1..597

( x i ) SEQUENCE DESCRIPTION: SEQ ID NO:1:

```
TCC  ACG  CCA  GGC  ATC  GTC  ATT  CCG  CCG  CAG  GAA  CAG  ATT  ACC  CAG  CAT       48
Ser  Thr  Pro  Gly  Ile  Val  Ile  Pro  Pro  Gln  Glu  Gln  Ile  Thr  Gln  His
 1                    5                        10                       15

GGC  AGC  CCC  TAT  GGA  CGC  TGC  GCG  AAC  AAG  ACC  CGT  GCC  CTG  ACC  GTG       96
Gly  Ser  Pro  Tyr  Gly  Arg  Cys  Ala  Asn  Lys  Thr  Arg  Ala  Leu  Thr  Val
               20                        25                       30

GCG  GAA  TTG  CGC  GGC  AGC  GGC  GAT  CTG  CAG  GAG  TAC  CTG  CGT  CAT  GTG      144
Ala  Glu  Leu  Arg  Gly  Ser  Gly  Asp  Leu  Gln  Glu  Tyr  Leu  Arg  His  Val
          35                        40                       45

ACG  CGC  GGC  TGG  TCA  ATA  TTT  GCG  CTC  TAC  GAT  GGC  ACC  TAT  CTC  GGC      192
Thr  Arg  Gly  Trp  Ser  Ile  Phe  Ala  Leu  Tyr  Asp  Gly  Thr  Tyr  Leu  Gly
     50                        55                       60

GGC  GAA  TAT  GGC  GGC  GTG  ATC  AAG  GAC  GGA  ACA  CCC  GGC  GGC  GCA  TTC      240
Gly  Glu  Tyr  Gly  Gly  Val  Ile  Lys  Asp  Gly  Thr  Pro  Gly  Gly  Ala  Phe
 65                       70                       75                       80

GAC  CTG  AAA  ACG  ACG  TTC  TGC  ATC  ATG  ACC  ACG  CGC  AAT  ACG  GGT  CAA      288
Asp  Leu  Lys  Thr  Thr  Phe  Cys  Ile  Met  Thr  Thr  Arg  Asn  Thr  Gly  Gln
                    85                       90                       95

CCC  GCA  ACG  GAT  CAC  TAC  TAC  AGC  AAC  GTC  ACC  GCC  ACT  CGC  CTG  CTC      336
Pro  Ala  Thr  Asp  His  Tyr  Tyr  Ser  Asn  Val  Thr  Ala  Thr  Arg  Leu  Leu
               100                      105                      110

TCC  AGC  ACC  AAC  AGC  AGG  CTA  TGC  GCG  GTC  TTC  GTC  AGA  AGC  GGG  CAA      384
Ser  Ser  Thr  Asn  Ser  Arg  Leu  Cys  Ala  Val  Phe  Val  Arg  Ser  Gly  Gln
```

|     |     |     | 115 |     |     |     |     | 120 |     |     |     |     | 125 |     |     |     |     |
|-----|-----|-----|-----|-----|-----|-----|-----|-----|-----|-----|-----|-----|-----|-----|-----|-----|-----|
| CCG | GTC | ATT | GGC | GCC | TGC | ACC | AGC | CCG | TAT | GAC | GGC | AAG | TAC | TGG | AGC | 432 |
| Pro | Val | Ile | Gly | Ala | Cys | Thr | Ser | Pro | Tyr | Asp | Gly | Lys | Tyr | Trp | Ser |     |
|     | 130 |     |     |     |     | 135 |     |     |     |     | 140 |     |     |     |     |     |
| ATG | TAC | AGC | CGG | CTG | CGG | AAA | ATG | CTT | TAC | CTG | ATC | TAC | GTG | GCC | GGC | 480 |
| Met | Tyr | Ser | Arg | Leu | Arg | Lys | Met | Leu | Tyr | Leu | Ile | Tyr | Val | Ala | Gly |     |
| 145 |     |     |     |     | 150 |     |     |     |     | 155 |     |     |     |     | 160 |     |
| ATC | TCC | GTA | CGC | GTC | CAT | GTC | AGC | AAG | GAA | GAA | CAG | TAT | TAC | GAC | TAT | 528 |
| Ile | Ser | Val | Arg | Val | His | Val | Ser | Lys | Glu | Glu | Gln | Tyr | Tyr | Asp | Tyr |     |
|     |     |     |     | 165 |     |     |     |     | 170 |     |     |     |     | 175 |     |     |
| GAG | GAC | GCA | ACG | TTC | GAG | ACT | TAC | GCC | CTT | ACC | GGC | ATC | TCC | ATC | TGC | 576 |
| Glu | Asp | Ala | Thr | Phe | Glu | Thr | Tyr | Ala | Leu | Thr | Gly | Ile | Ser | Ile | Cys |     |
|     |     |     | 180 |     |     |     |     | 185 |     |     |     |     | 190 |     |     |     |
| AAT | CCT | GGA | TCA | TCC | TTA | TGC |     |     |     |     |     |     |     |     |     | 597 |
| Asn | Pro | Gly | Ser | Ser | Leu | Cys |     |     |     |     |     |     |     |     |     |     |
|     |     | 195 |     |     |     |     |     |     |     |     |     |     |     |     |     |     |

( 2 ) INFORMATION FOR SEQ ID NO:2:

( i ) SEQUENCE CHARACTERISTICS:
        ( A ) LENGTH: 199 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

| Ser | Thr | Pro | Gly | Ile | Val | Ile | Pro | Pro | Gln | Glu | Gln | Ile | Thr | Gln | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gly | Ser | Pro | Tyr | Gly | Arg | Cys | Ala | Asn | Lys | Thr | Arg | Ala | Leu | Thr | Val |
|     |     |     | 20  |     |     |     |     | 25  |     |     |     |     | 30  |     |     |
| Ala | Glu | Leu | Arg | Gly | Ser | Gly | Asp | Leu | Gln | Glu | Tyr | Leu | Arg | His | Val |
|     |     | 35  |     |     |     |     | 40  |     |     |     |     | 45  |     |     |     |
| Thr | Arg | Gly | Trp | Ser | Ile | Phe | Ala | Leu | Tyr | Asp | Gly | Thr | Tyr | Leu | Gly |
|     | 50  |     |     |     |     | 55  |     |     |     |     | 60  |     |     |     |     |
| Gly | Glu | Tyr | Gly | Gly | Val | Ile | Lys | Asp | Gly | Thr | Pro | Gly | Gly | Ala | Phe |
| 65  |     |     |     |     | 70  |     |     |     |     | 75  |     |     |     |     | 80  |
| Asp | Leu | Lys | Thr | Thr | Phe | Cys | Ile | Met | Thr | Thr | Arg | Asn | Thr | Gly | Gln |
|     |     |     |     | 85  |     |     |     |     | 90  |     |     |     |     | 95  |     |
| Pro | Ala | Thr | Asp | His | Tyr | Tyr | Ser | Asn | Val | Thr | Ala | Thr | Arg | Leu | Leu |
|     |     |     | 100 |     |     |     |     | 105 |     |     |     |     | 110 |     |     |
| Ser | Ser | Thr | Asn | Ser | Arg | Leu | Cys | Ala | Val | Phe | Val | Arg | Ser | Gly | Gln |
|     |     | 115 |     |     |     |     | 120 |     |     |     |     | 125 |     |     |     |
| Pro | Val | Ile | Gly | Ala | Cys | Thr | Ser | Pro | Tyr | Asp | Gly | Lys | Tyr | Trp | Ser |
|     | 130 |     |     |     |     | 135 |     |     |     |     | 140 |     |     |     |     |
| Met | Tyr | Ser | Arg | Leu | Arg | Lys | Met | Leu | Tyr | Leu | Ile | Tyr | Val | Ala | Gly |
| 145 |     |     |     |     | 150 |     |     |     |     | 155 |     |     |     |     | 160 |
| Ile | Ser | Val | Arg | Val | His | Val | Ser | Lys | Glu | Glu | Gln | Tyr | Tyr | Asp | Tyr |
|     |     |     |     | 165 |     |     |     |     | 170 |     |     |     |     | 175 |     |
| Glu | Asp | Ala | Thr | Phe | Glu | Thr | Tyr | Ala | Leu | Thr | Gly | Ile | Ser | Ile | Cys |
|     |     |     | 180 |     |     |     |     | 185 |     |     |     |     | 190 |     |     |
| Asn | Pro | Gly | Ser | Ser | Leu | Cys |     |     |     |     |     |     |     |     |     |
|     |     | 195 |     |     |     |     |     |     |     |     |     |     |     |     |     |

( 2 ) INFORMATION FOR SEQ ID NO:3:

( i ) SEQUENCE CHARACTERISTICS:
        ( A ) LENGTH: 597 base pairs
        ( B ) TYPE: nucleic acid
        ( C ) STRANDEDNESS: single (D) TOPOLOGY: linear (ii) MOLECULE TYPE: cDNA (ix) FEATURE:
    (A) NAME/KEY: CDS
    (B) LOCATION: 1..597

(xi) SEQUENCE DESCRIPTION: SEQ ID NO:3:

| GTT | GCG | CCA | GGC | ATC | GTC | ATC | CCG | CCG | AAG | GCA | CTG | TTC | ACC | CAA | CAG | 48 |
|---|---|---|---|---|---|---|---|---|---|---|---|---|---|---|---|---|
| Val | Ala | Pro | Gly | Ile | Val | Ile | Pro | Pro | Lys | Ala | Leu | Phe | Thr | Gln | Gln | |
| 200 | | | | 205 | | | | | 210 | | | | | | 215 | |

| GGC | GGC | GCC | TAT | GGA | CGC | TGC | CCG | AAC | GGA | ACC | CGC | GCC | TTG | ACC | GTG | 96 |
|---|---|---|---|---|---|---|---|---|---|---|---|---|---|---|---|---|
| Gly | Gly | Ala | Tyr | Gly | Arg | Cys | Pro | Asn | Gly | Thr | Arg | Ala | Leu | Thr | Val | |
| | | | | 220 | | | | | 225 | | | | | 230 | | |

| GCC | GAA | CTG | CGC | GGC | AAC | GCC | GAA | TTG | CAG | ACG | TAT | TTG | CGC | CAG | ATA | 144 |
|---|---|---|---|---|---|---|---|---|---|---|---|---|---|---|---|---|
| Ala | Glu | Leu | Arg | Gly | Asn | Ala | Glu | Leu | Gln | Thr | Tyr | Leu | Arg | Gln | Ile | |
| | | | 235 | | | | | 240 | | | | | 245 | | | |

| ACG | CCC | GGC | TGG | TCC | ATA | TAC | GGT | CTC | TAT | GAC | GGT | ACG | TAC | CTG | GGC | 192 |
|---|---|---|---|---|---|---|---|---|---|---|---|---|---|---|---|---|
| Thr | Pro | Gly | Trp | Ser | Ile | Tyr | Gly | Leu | Tyr | Asp | Gly | Thr | Tyr | Leu | Gly | |
| | | 250 | | | | 255 | | | | | 260 | | | | | |

| CAG | GCG | TAC | GGC | GGC | ATC | ATC | AAG | GAC | GCG | CCG | CCA | GGC | GCG | GGG | TTC | 240 |
|---|---|---|---|---|---|---|---|---|---|---|---|---|---|---|---|---|
| Gln | Ala | Tyr | Gly | Gly | Ile | Ile | Lys | Asp | Ala | Pro | Pro | Gly | Ala | Gly | Phe | |
| 265 | | | | | 270 | | | | | | 275 | | | | | |

| ATT | TAT | CGC | GAA | ACT | TTC | TGC | ATC | ACG | ACC | ATA | TAC | AAG | ACC | GGG | CAA | 288 |
|---|---|---|---|---|---|---|---|---|---|---|---|---|---|---|---|---|
| Ile | Tyr | Arg | Glu | Thr | Phe | Cys | Ile | Thr | Thr | Ile | Tyr | Lys | Thr | Gly | Gln | |
| 280 | | | | | 285 | | | | | 290 | | | | | 295 | |

| CCG | GCT | GCG | GAT | CAC | TAC | TAC | AGC | AAG | GTC | ACG | GCC | ACG | CGC | CTG | CTC | 336 |
|---|---|---|---|---|---|---|---|---|---|---|---|---|---|---|---|---|
| Pro | Ala | Ala | Asp | His | Tyr | Tyr | Ser | Lys | Val | Thr | Ala | Thr | Arg | Leu | Leu | |
| | | | | 300 | | | | | 305 | | | | | 310 | | |

| GCC | AGC | ACC | AAC | AGC | AGG | CTG | TGC | GCG | GTA | TTC | GTC | AGG | GAC | GGG | CAA | 384 |
|---|---|---|---|---|---|---|---|---|---|---|---|---|---|---|---|---|
| Ala | Ser | Thr | Asn | Ser | Arg | Leu | Cys | Ala | Val | Phe | Val | Arg | Asp | Gly | Gln | |
| | | | 315 | | | | | 320 | | | | | 325 | | | |

| TCG | GTC | ATC | GGA | GCC | TGC | GCC | AGC | CCG | TAT | GAA | GGC | AGG | TAC | AGA | GAC | 432 |
|---|---|---|---|---|---|---|---|---|---|---|---|---|---|---|---|---|
| Ser | Val | Ile | Gly | Ala | Cys | Ala | Ser | Pro | Tyr | Glu | Gly | Arg | Tyr | Arg | Asp | |
| | | 330 | | | | 335 | | | | | 340 | | | | | |

| ATG | TAC | GAC | GCG | CTG | CGG | CGC | CTG | CTG | TAC | ATG | ATC | TAT | ATG | TCC | GGC | 480 |
|---|---|---|---|---|---|---|---|---|---|---|---|---|---|---|---|---|
| Met | Tyr | Asp | Ala | Leu | Arg | Arg | Leu | Leu | Tyr | Met | Ile | Tyr | Met | Ser | Gly | |
| | 345 | | | | 350 | | | | | 355 | | | | | | |

| CTT | GCC | GTA | CGC | GTC | CAC | GTC | AGC | AAG | GAA | GAG | CAG | TAT | TAC | GAC | TAC | 528 |
|---|---|---|---|---|---|---|---|---|---|---|---|---|---|---|---|---|
| Leu | Ala | Val | Arg | Val | His | Val | Ser | Lys | Glu | Glu | Gln | Tyr | Tyr | Asp | Tyr | |
| 360 | | | | | 365 | | | | | 370 | | | | | 375 | |

| GAG | GAC | GCC | ACA | TTC | CAG | ACC | TAT | GCC | CTC | ACC | GGC | ATT | TCC | CTC | TGC | 576 |
|---|---|---|---|---|---|---|---|---|---|---|---|---|---|---|---|---|
| Glu | Asp | Ala | Thr | Phe | Gln | Thr | Tyr | Ala | Leu | Thr | Gly | Ile | Ser | Leu | Cys | |
| | | | | 380 | | | | | 385 | | | | | 390 | | |

| AAC | CCG | GCA | GCG | TCG | ATA | TGC | | | | | | | | | | 597 |
|---|---|---|---|---|---|---|---|---|---|---|---|---|---|---|---|---|
| Asn | Pro | Ala | Ala | Ser | Ile | Cys | | | | | | | | | | |
| | | | 395 | | | | | | | | | | | | | |

(2) INFORMATION FOR SEQ ID NO:4:

(i) SEQUENCE CHARACTERISTICS:
    (A) LENGTH: 199 amino acids
    (B) TYPE: amino acid
    (D) TOPOLOGY: linear (ii) MOLECULE TYPE: protein (xi) SEQUENCE DESCRIPTION: SEQ ID NO:4:

| Val | Ala | Pro | Gly | Ile | Val | Ile | Pro | Pro | Lys | Ala | Leu | Phe | Thr | Gln | Gln |
|---|---|---|---|---|---|---|---|---|---|---|---|---|---|---|---|
| 1 | | | | 5 | | | | | 10 | | | | | 15 | |

| Gly | Gly | Ala | Tyr | Gly | Arg | Cys | Pro | Asn | Gly | Thr | Arg | Ala | Leu | Thr | Val |
|---|---|---|---|---|---|---|---|---|---|---|---|---|---|---|---|
| | | | 20 | | | | | 25 | | | | | 30 | | |

```
Ala  Glu  Leu  Arg  Gly  Asn  Ala  Glu  Leu  Gln  Thr  Tyr  Leu  Arg  Gln  Ile
          35                       40                       45

Thr  Pro  Gly  Trp  Ser  Ile  Tyr  Gly  Leu  Tyr  Asp  Gly  Thr  Tyr  Leu  Gly
     50                       55                       60

Gln  Ala  Tyr  Gly  Gly  Ile  Ile  Lys  Asp  Ala  Pro  Pro  Gly  Ala  Gly  Phe
65                            70                       75                       80

Ile  Tyr  Arg  Glu  Thr  Phe  Cys  Ile  Thr  Thr  Ile  Tyr  Lys  Thr  Gly  Gln
               85                       90                       95

Pro  Ala  Ala  Asp  His  Tyr  Tyr  Ser  Lys  Val  Thr  Ala  Thr  Arg  Leu  Leu
               100                      105                      110

Ala  Ser  Thr  Asn  Ser  Arg  Leu  Cys  Ala  Val  Phe  Val  Arg  Asp  Gly  Gln
               115                      120                      125

Ser  Val  Ile  Gly  Ala  Cys  Ala  Ser  Pro  Tyr  Glu  Gly  Arg  Tyr  Arg  Asp
     130                      135                      140

Met  Tyr  Asp  Ala  Leu  Arg  Arg  Leu  Leu  Tyr  Met  Ile  Tyr  Met  Ser  Gly
145                           150                      155                      160

Leu  Ala  Val  Arg  Val  His  Val  Ser  Lys  Glu  Gln  Tyr  Tyr  Asp  Tyr
                    165                      170                      175

Glu  Asp  Ala  Thr  Phe  Gln  Thr  Tyr  Ala  Leu  Thr  Gly  Ile  Ser  Leu  Cys
               180                      185                      190

Asn  Pro  Ala  Ala  Ser  Ile  Cys
               195
```

( 2 ) INFORMATION FOR SEQ ID NO:5:

( i ) SEQUENCE CHARACTERISTICS:
        ( A ) LENGTH: 330 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: CDS
        ( B ) LOCATION: 1..330

( x i ) SEQUENCE DESCRIPTION: SEQ ID NO:5:

```
GAC  GTT  CCT  TAT  GTG  CTG  GTG  AAG  ACC  AAT  ATG  GTG  GTC  ACC  AGC  GTA        48
Asp  Val  Pro  Tyr  Val  Leu  Val  Lys  Thr  Asn  Met  Val  Val  Thr  Ser  Val
200                      205                      210                      215

GCC  ATG  AAG  CCG  TAT  GAA  GTC  ACC  CCG  ACG  CGC  ATG  CTG  GTC  TGC  GGC        96
Ala  Met  Lys  Pro  Tyr  Glu  Val  Thr  Pro  Thr  Arg  Met  Leu  Val  Cys  Gly
               220                      225                      230

ATC  GCC  GCC  AAA  CTG  GGC  GCC  GCG  GCC  AGC  AGC  CCG  GAC  GCG  CAC  GTG       144
Ile  Ala  Ala  Lys  Leu  Gly  Ala  Ala  Ala  Ser  Ser  Pro  Asp  Ala  His  Val
               235                      240                      245

CCG  TTC  TGC  TTC  GGC  AAG  GAT  CTC  AAG  CGT  CCC  GGC  AGC  AGT  CCC  ATG       192
Pro  Phe  Cys  Phe  Gly  Lys  Asp  Leu  Lys  Arg  Pro  Gly  Ser  Ser  Pro  Met
          250                      255                      260

GAA  GTC  ATG  TTG  CGC  GCC  GTC  TTC  ATG  CAA  CAA  CGG  CCG  CTG  CGC  ATG       240
Glu  Val  Met  Leu  Arg  Ala  Val  Phe  Met  Gln  Gln  Arg  Pro  Leu  Arg  Met
          265                      270                      275

TTT  CTG  GGT  CCC  AAG  CAA  CTC  ACT  TTC  GAA  GGC  AAG  CCC  GCG  CTC  GAA       288
Phe  Leu  Gly  Pro  Lys  Gln  Leu  Thr  Phe  Glu  Gly  Lys  Pro  Ala  Leu  Glu
280                      285                      290                      295

CTG  ATC  CGG  ATG  GTC  GAA  TGC  AGC  GGC  AAG  CAG  GAT  TGC  CCC                 330
Leu  Ile  Arg  Met  Val  Glu  Cys  Ser  Gly  Lys  Gln  Asp  Cys  Pro
               300                      305
```

( 2 ) INFORMATION FOR SEQ ID NO:6:

( i ) SEQUENCE CHARACTERISTICS:
  ( A ) LENGTH: 110 amino acids
  ( B ) TYPE: amino acid
  ( D ) TOPOLOGY: linear ( i i ) MOLECULE TYPE: protein ( x i ) SEQUENCE DESCRIPTION: SEQ ID NO:6:

```
Asp Val Pro Tyr Val Leu Val Lys Thr Asn Met Val Val Thr Ser Val
 1               5                  10                 15

Ala Met Lys Pro Tyr Glu Val Thr Pro Thr Arg Met Leu Val Cys Gly
            20                  25                 30

Ile Ala Ala Lys Leu Gly Ala Ala Ala Ser Ser Pro Asp Ala His Val
            35              40              45

Pro Phe Cys Phe Gly Lys Asp Leu Lys Arg Pro Gly Ser Ser Pro Met
    50              55              60

Glu Val Met Leu Arg Ala Val Phe Met Gln Gln Arg Pro Leu Arg Met
 65             70                  75                     80

Phe Leu Gly Pro Lys Gln Leu Thr Phe Glu Gly Lys Pro Ala Leu Glu
            85                  90                 95

Leu Ile Arg Met Val Glu Cys Ser Gly Lys Gln Asp Cys Pro
            100                 105                110
```

( 2 ) INFORMATION FOR SEQ ID NO:7:

( i ) SEQUENCE CHARACTERISTICS:
    ( A ) LENGTH: 300 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 1..300

( x i ) SEQUENCE DESCRIPTION: SEQ ID NO:7:

```
GCC GGC TTG CCG ACC CAT CTG TAC AAG AAC TTC ACT GTC CAG GAG CTG      48
Ala Gly Leu Pro Thr His Leu Tyr Lys Asn Phe Thr Val Gln Glu Leu
            115                 120                 125

GCC TTG AAA CTG AAG GGC AAG AAT CAG GAG TTC TGC CTG ACC GCC TTC      96
Ala Leu Lys Leu Lys Gly Lys Asn Gln Glu Phe Cys Leu Thr Ala Phe
            130                 135                 140

ATG TCG GGC AGA AGC CTG GTC CGG GCG TGC CTG TCC GAC GCG GGA CAC     144
Met Ser Gly Arg Ser Leu Val Arg Ala Cys Leu Ser Asp Ala Gly His
            145                 150                 155

GAG CAC GAC ACG TGG TTC GAC ACC ATG CTT GGC TTT GCC ATA TCC GCG     192
Glu His Asp Thr Trp Phe Asp Thr Met Leu Gly Phe Ala Ile Ser Ala
    160                 165                 170

TAT GCG CTC AAG AGC CGG ATC GCG CTG ACG GTG GAA GAC TCG CCG TAT     240
Tyr Ala Leu Lys Ser Arg Ile Ala Leu Thr Val Glu Asp Ser Pro Tyr
175                 180                 185                 190

CCG GGC ACT CCC GGC GAT CTG CTC GAA CTG CAG ATC TGC CCG CTC AAC     288
Pro Gly Thr Pro Gly Asp Leu Leu Glu Leu Gln Ile Cys Pro Leu Asn
                195                 200                 205

GGA TAT TGC GAA                                                     300
Gly Tyr Cys Glu
            210
```

( 2 ) INFORMATION FOR SEQ ID NO:8:

( i ) SEQUENCE CHARACTERISTICS:

( A ) LENGTH: 100 amino acids
( B ) TYPE: amino acid
( D ) TOPOLOGY: linear ( i i ) MOLECULE TYPE: protein ( x i ) SEQUENCE DESCRIPTION: SEQ ID NO:8:

| Ala | Gly | Leu | Pro | Thr | His | Leu | Tyr | Lys | Asn | Phe | Thr | Val | Gln | Glu | Leu |
|---|---|---|---|---|---|---|---|---|---|---|---|---|---|---|---|
| 1 | | | | 5 | | | | | 10 | | | | | 15 | |
| Ala | Leu | Lys | Leu | Lys | Gly | Lys | Asn | Gln | Glu | Phe | Cys | Leu | Thr | Ala | Phe |
| | | | 20 | | | | | 25 | | | | | 30 | | |
| Met | Ser | Gly | Arg | Ser | Leu | Val | Arg | Ala | Cys | Leu | Ser | Asp | Ala | Gly | His |
| | | 35 | | | | | 40 | | | | | 45 | | | |
| Glu | His | Asp | Thr | Trp | Phe | Asp | Thr | Met | Leu | Gly | Phe | Ala | Ile | Ser | Ala |
| | 50 | | | | | 55 | | | | | 60 | | | | |
| Tyr | Ala | Leu | Lys | Ser | Arg | Ile | Ala | Leu | Thr | Val | Glu | Asp | Ser | Pro | Tyr |
| 65 | | | | | 70 | | | | | 75 | | | | | 80 |
| Pro | Gly | Thr | Pro | Gly | Asp | Leu | Leu | Glu | Leu | Gln | Ile | Cys | Pro | Leu | Asn |
| | | | | 85 | | | | | 90 | | | | | 95 | |
| Gly | Tyr | Cys | Glu | | | | | | | | | | | | |
| | | | 100 | | | | | | | | | | | | |